United States Patent [19]
Davies-Heerema et al.

[11] Patent Number: 5,976,817
[45] Date of Patent: Nov. 2, 1999

[54] DIAGNOSTIC METHOD FOR DETECTING ALZHEIMER'S DISEASE IN LIVING PATIENTS

[75] Inventors: Theresa A. Davies-Heerema, Boston; Elizabeth R. Simons, West Newton, both of Mass.

[73] Assignee: Trustees of Boston University, Boston, Mass.

[21] Appl. No.: 08/742,830

[22] Filed: Oct. 31, 1996

[51] Int. Cl.$^6$ ................................................ G01N 33/53
[52] U.S. Cl. .................. 435/7.21; 435/7.94; 435/7.95; 436/503; 436/519; 436/811
[58] Field of Search .................... 435/6, 7.1, 7.2, 435/7.21, 7.24, 7.9, 7.92, 7.94, 7.95, 287.2, 287.3; 436/5.8, 5.9, 536, 538, 501, 503, 63, 811

[56] References Cited

U.S. PATENT DOCUMENTS

5,213,962  5/1993  Van Nostrand et al. .
5,270,165  12/1993  Van Nostrand et al. .

OTHER PUBLICATIONS

Li et al., Blood, vol. 84, No. 1, pp. 133–142, Jul. 1, 1994.
Davies et al, Society for Neuroscience, 22(1–3), Sep. 16, 1996.
Gardella et al, Blood, 67(3):303–313. 1992.
Davies et al., *Neurobiology of Aging* 18(2): 147–153 (1997).
Davies et al., *J. of Lab. and Clin. Medicine* 130(1): 21–32 (1997).
Van Nostrand et al., *Science* 248, No. 4956: 745–748 (1990).
Bush et al., *J. Biol. Chem* 265(26): 15977–15983 (1990).
Rao et al., *Indian J. of Physio. and Pharm.* 40(1): 5–14 (1996).
Ciallella et al., *J. of Neuro. Res.* 37(6): 769–776 (1994).

*Primary Examiner*—Patricia Duffy
*Attorney, Agent, or Firm*—Kevin M. Farrell

[57] ABSTRACT

Upon activation, platelet α-granules' soluble contents are secreted and membrane-bound contents are translocated to the plasma membrane. Membrane-bound proteins include the β-amyloid precursor protein (APP) from which the β-amyloid (Aβ) deposits found surrounding the cerebrovasculature of patients with Alzheimer's Disease (AD) may originate. It has been discovered that activated platelets from AD patients exhibit less APP processing, retain more of the protein on their surface and secrete less as soluble fragments, than do controls. There is little APP or CD62 on the surface of resting platelets, but upon activation, while control platelets exhibited more of both proteins on their surface, advanced AD patients exhibited CD62 in similar amounts to controls, but retained significantly more surface APP. AD platelets secreted similar amounts of most soluble α-granule contents as controls, but less APP fragments. These results indicate a processing defect which may be used in screening assays to help identify patients with Alzheimer's disease.

7 Claims, 5 Drawing Sheets

FIG. 1

FIG. 2A — CONTROL

FIG. 2B — AGE-MATCHED

FIG. 2C — ALZHEIMER'S DISEASE

FIG. 2D — PICK'S DISEASE

… imer's disease in a patient by obtaining, from the patient, a blood sample containing platelets, activating the platelets (preferably by treating them with α-thrombin), separating degranulated platelets from the proteins secreted by degranulation (by, e.g., centrifugation, molecular sieve chromatography or flow cytometry); labeling the outer membrane of degranulated platelets with a label that specifically binds to at least a portion of amyloid precursor protein (APP); and determining the amount of label attached to the outer membrane of the activated platelets of the patient. Of course, the labeling, separating and determining may be combined if flow cytometry is used as the separation technique. An increase in the amount of APP, or fragments thereof, attached to the outer membrane of the activated platelets of the patient, relative to the average amount of APP or fragments thereof attached to the outer membrane of the activated platelets of control persons, is indicative of Alzheimer's disease in the patient. In one alternative, an increase in the amount of APP attached to the membrane of activated platelets may be determined by comparing the amount of APP in the platelet fraction before and after activation to the before-and-after amounts of CD62.

The present studies, using platelets from a group of male patients as well as some female patients, all diagnosed as having advanced Alzheimer's disease (AD), compare the secreted and translocated products in washed platelets from these patients with those from nondemented individuals of either comparable (AM) or younger (C) age. Functional assays of neutrophils from the same individuals were used as internal controls and indicated no differences between the patient and control groups. These studies demonstrate that AD patients' platelets exhibit defective processing of APP, detected as a retention of apparently intact APP on their plasma membrane. This is a defect specific to APP, unrelated to degranulation per se, since the secretion of soluble α-granule contents as well as translocation of another α-granule membrane protein, CD62, was indistinguishable from those of controls.

DETAILED DESCRIPTION OF THE INVENTION AND PARTICULAR EMBODIMENTS

Davies, et al. (1993), *Biochem. Biophys. Res. Comm.*, 194:537–543, described platelet responses to thrombin stimulation as: (a) increase in cytoplasmic calcium ion; (b) membrane depolarization; (c) transient acidification followed by alkalinization of the cytoplasm; and (d) degranulation, including sequential release of dense granule contents, α-granule contents (including APP), and lysosomal granule contents. The extent of acidification in platelets of probable Alzheimer's disease patients was reported to exceed that of control platelets, but no mechanism for this effect or consequential effects on proteolytic processing of APP was described.

It has now been discovered that this hyperacidification defect is correlated with the known risk factor Apolipoprotein E4. Furthermore, by three separate analyses (flow cytometry, ELISA assay and Western blotting), platelets from patients with advanced AD exhibit both a hyperacidification signal transduction defect and a decreased APP processing capability. These platelets therefore retain significantly more membrane-bound APP on their surface after activation than platelets of non-demented individuals or patients with Pick's disease, and they release less soluble APP fragments (sAPP). The defect is specific for AD platelets and appears to affect only APP proteolysis, since translocation of other α-granule membrane proteins such as CD62, and secretion of soluble granule contents (serotonin, platelet factor 4 and β-glucuronidase) did not differ from controls. Since control platelets retain less APP on activation, but contain the same amount of APP in the resting state as platelets from patients with AD, the implication is that APP was already processed into soluble fragments in the resting platelet. Platelets are formed from megakaryocytes, and it is therefore possible that this APP cleavage took place at the megakaryocyte level. These findings therefore imply that the AD patients' platelets have an APP proteolytic processing defect, either while the platelets (or their precursor megakaryocytes) are in the resting state, or within 5 minutes after activation.

This invention provides screening assays that can help in diagnosing Alzheimer's disease by determining the degree to which a patient's platelets exhibit defective APP processing. Typically the defect is demonstrated when uncleaved APP is exhibited on the plasma membrane of activated platelets (i.e., mAPP—which is detectable as full length APP or at least a membrane-bound fragment of APP). The procedure by which the relative amount of uncleaved APP retained on platelet membranes after activation is determined is not critical to this invention, so long as it can be confirmed that mAPP is bound to the plasma membrane in increased amount over what would be expected for normal individuals (non-Alzheimer's).

Granule membrane proteins are not detectable on the surface of resting platelets because these have not yet degranulated. When the platelets are activated these granule membrane proteins, like mAPP, CD62 and CD63, are translocated to the outer (plasma) membrane of the platelet where they are now detectable, i.e. "expressed". CD62 and CD63 can be measured as controls to be sure that there is nothing abnormal about the platelet activation process itself in the patients and controls. In contrast, while activated platelets from advanced AD patients still retain much APP on the plasma membrane, controls (non-Alzheimer individuals) appear to retain little mAPP. This implies that, since control and AD patient platelets contain the same amount of total APP, the mAPP was pre-cleaved in the non-AD controls' platelets, and hence was released with other soluble granule contents upon activation.

The defective cleavage in the AD patients could leave essentially intact, i.e. full length, mAPP, or partially cleaved membrane bound protein cleaved at the β-secretase (N-terminal of Aβ), α-secretase (between residues 16 and 17 of Aβ) or γ-secretase (at residues 39 to 42 of Aβ) sites. These alternatives may be distinguished by using, on the same activated platelet samples, antibodies to intact mAPP (i.e., 22C11, anti-N-terminal), to the 1–17 and to the 17–28 Aβ fragments. If a γ-secretase was defective, one would expect a constant ratio of binding for the three antibodies, because the extracellular portion of APP is either there (all 3 antibodies bind) if the γ-secretase is inactive or cleaved at 39–42 (none of the three antibodies bind) if the γ-secretase is active. If there were a defect in the α-secretase, but an active β-secretase, less 22C11 would bind but the ratio of anti-1-17/anti-17–28 would be constant. If the β-secretase were not functioning (the condition which would not yield the damaging Aβ, i.e. the non-amyloidogenic condition expected in controls), a lower ratio of anti-1-17/anti-17–28 would be found because the α-secretase would have left the fragment starting at residue 17 membrane-bound. In actuality, virtually no such "stubs" are seen, implying that once there has been either α- or β-secretase cleavage, the γ-secretase cleaves the remaining fragment very rapidly. For this reason, the advanced AD patients' platelets could have more than one defective secretase (non-functional α- and/or β-secretase).

SAMPLING

Patient samples for diagnostic testing according to this invention may be obtained in any manner which provides platelets suitable for analysis as described herein. Typically, the sample will be a blood sample enriched in platelets after the blood is removed from the patient. Preferably, the platelets will be resting platelets, so that a portion of the platelets can be activated and compared to the resting platelets as described below.

In a particular preferred mode, blood is drawn, usually from the antecubital vein in the crook of the arm, as it is by clinical laboratories for most routine blood tests, into a vacutainer containing an anticoagulant, isotonic citrate. All remaining steps are performed ex vivo. There is no risk to the donor except for the slight discomfort of a needle prick. The sample is centrifuged at low speed to sediment the red cells. The supernatant (known as platelet-rich plasma) is removed and layered onto a small Sepharose 2B column equilibrated with an isotonic buffer at pH 7.4 (HEPES or PBS, phosphate-buffered saline). More buffer is used to elute the platelets, which are then counted. The assays typically use $3 \times 10^7$ platelets/ml buffer.

While it may be possible to obtain from the patient platelets which have been activated endogenously, this is less preferable for at least two reasons. First, activation usually occurs locally by contact with a lesion; activated platelets are very "sticky," adhering to exposed collagen, and therefore will no longer be circulating. Obtaining a sample of these platelets would be difficult. Secondly, increased APP on the activated platelet membrane would be determined by comparison to an external standard, while a sample of resting platelets can serve as its own standard for comparison to an aliquot of the sample which is activated ex vivo, as described below.

PLATELET ACTIVATION/DEGRANULATION

The assay of this invention involves determining whether full length APP is translocated to the plasma membrane when platelets are stimulated to secrete the contents of various granules (e.g., dense granules, α-granules, lysosomal granules). Platelet degranulation can be stimulated by a variety of factors which are known in the art to stimulate activation of platelets, including ADP, collagen and epinephrine. However, α-thrombin is the most potent physiological stimulus of platelets, as well as the stimulus which is most stable and whose concentration and effect are most reproducible. Therefore, the preferred method of activation is treating the platelets with α-thrombin. Usually treatment of platelets with at least 4.5 nM α-thrombin is sufficient. Suitable treatment conditions are 9 nM α-thrombin, $3 \times 10^7$ platelets per ml, at pH 7.4 and 37° C., or conditions that induce similar extent of degranulation.

It should be noted that no difference in the amount of APP retained on the plasma membrane of platelets from patients with AD has been detected, whether or not thrombin remains in contact with the platelets or is inhibited by hirudin, a specific thrombin inhibitor, added 10 seconds after thrombin and hence before translocation has occurred. Under these conditions, membrane-bound APP is therefore not cleaved by thrombin; the flow cytometric studies clearly do not permit determination of whether secreted soluble APP fragments are subject to thrombinolysis, but Western blots imply that they are not. These results thus differ from reports in the literature (Davis-Salinas, et al. (1994) *J. Biol. Chem.*, 269:22623–22637; Igarashi, et al. (1992), *Biochem. Biophys. Res. Comm.*, 185:1000–1004) that APP is a thrombin substrate, but both of the published studies utilized very different conditions, soluble APP and higher thrombin concentrations.

A sample in which platelet degranulation has been carried out will contain a cellular fraction, containing the activated platelets (and platelet plasma membranes) and an extracellular fraction, containing the secreted peptides. In platelets from Alzheimer's patients, the level of soluble APP (sAPP) in the extracellular fraction is lower and the level of membrane bound APP (mAPP) in the cellular fraction is higher than in non-Alzheimer's platelets. Either the level of sAPP or the level of mAPP can be measured in the activated platelet sample, but it is preferable to measure the mAPP level. This measurement is usually more sensitive.

For some detection procedures, the cellular fraction is separated from the extracellular fraction before attempting to detect APP. Techniques for effecting this separation will be readily apparent to the skilled artisan, and may include micro filtration through membranes or molecular sieves with pores which will allow sAPP to pass but not membrane vesicles, or centrifugation through a density gradient. A preferred separation method is differential centrifugation, in which the cellular fraction is recovered as a pellet and the extracellular fraction as supernate. After separation of the fractions, measurement of APP in the respective fraction can be carried out without significant contamination by APP from the other fraction (which is important, since AD is correlated with shift in APP from one fraction to the other without change in the total APP level).

DETECTING APP

Measurement of APP in the respective fractions could be accomplished by quantitating the amount of protein of the appropriate molecular weight (110–125 kDa for sAPP; 130–140 kDa for mAPP). Such measurements can be performed by electrophoresis, molecular sieve chromatography, and other well known procedures for fractionating proteins by size. Generally such procedures will be carried out after denaturing proteins in the fraction, preferably in a detergent solution. However, use of antibodies which specifically bind epitopes on the respective proteins is generally preferred.

As used herein, the term "antibodies" includes all types of immunoglobulin molecules, monoclonal antibodies, polyclonal antibodies, affinity-purified polyclonal antibodies, Fab and (Fab)$_2$, single-chain (SC) antibodies, or other molecules which specifically bind an epitope on APP in a manner comparable to the manner in which particular monoclonal antibodies used in the Examples below bind to their epitopes. Generally, the antibodies used to detect APP according to this invention will be labeled with a detectable label, such as a radiolabel, a fluorescent label, second antibody specific for the anti-APP antibody where the second antibody is conjugated to an enzyme, etc.

Many suitable techniques for using such antibodies to detect APP epitopes will be apparent to the skilled artisan, including fluorescence activated cell sorting (FACS), sandwich assays, competitive immunoassays, ELISA assays, Western blots, dot blots, ouchterlony plates, immunoelectrophoresis, fluorimetry, microcopy, fluorescence microscopy, ultra-filtration (using radiolabeled antibodies) and others. While any antibody which specifically binds to an epitope on APP is potentially useful in the assays of this invention, antibodies which bind to epitopes within Aβ cleaved by the proteolytic step that releases sAPP will, of course, not be used for detection of sAPP. On the other hand, antibodies specific for an epitope within Aβ which is cleaved during APP processing in normal individuals will be particularly preferred for detection of retained APP in Alzheimer's patients. Alternatively, antibodies which specifically bind to an epitope on the N-terminal portion of APP are also particularly preferred for detecting retained APP. Suitable antibodies include: (1) mAb 22C11 from Boehringer-Mannheim which recognizes the extra cytoplasmic N-terminal domain of APP and can be used to detect secreted sAPP and near-full-length membrane-bound forms, (2) two antibodies (pAb 1–17 and pAb 17–28) to residues 1–17 and 17–28 of Aβ made by Quality Controlled Biochemicals Inc. (Hopkinton, Mass.) recognizing Aβ, specifically distinguishing between cleavages at the α- or β-secretase site and (3) Ab 6E10 to Aβ 1–17 and mAb 4G8 to Aβ 17–24, commercially available from Senetek.

In a preferred embodiment, the sample of activated platelets is analyzed by FACS using antibodies specific for an epitope on Aβ which is cleaved during APP processing in normal individuals or antibodies which specifically bind to an epitope on APP N-terminal to amyloid β-peptide (Aβ). In this embodiment, a step for separating the cellular and extracellular fractions prior to preparation of the sample for FACS analysis is unnecessary.

A fluorescence activated cell sorter (or flow cytometer) only measures the fluorescence of the individual cells as they drop past the interrogating laser, and does not record any fluorescence of the suspending buffer solution since it has been enormously diluted (by a factor of at least 1000) by the flowing sheath buffer. On the other hand, in suspension fluorimetry the fluorescence of both the cells and the suspending medium is recorded simultaneously.

Determination of whether the levels of sAPP and mAPP have decreased and increased, respectively, can be accomplished in various ways. Typically, the levels will be determined for the patient and compared to an average level for age-matched controls. Alternatively, the level of CD62 in platelets may be measured in the same patient's platelets for resting and activated states, and the ratio compared to the ratio of mAPP resting:activated.

The levels of mAPP and/or CD62, both of which remain as membrane proteins with the activated platelets, can be measured by a number of ways, all involving the use of specific antibodies to the individual proteins:

a) flow cytometry of intact activated platelets, using either fluorescently labeled mono- or polyclonal anti-APP, anti-Aβ, and/or anti-CD62 "primary" antibodies, or unlabeled monoclonal primary antibodies followed by fluorescently labeled "secondary" antibodies to the monoclonal IgG (e.g. a mouse monoclonal like 22C11, followed by a fluorescein-labeled anti-mouse IgG);

b) Western blots of SDS gels of detergent-solubilized activated platelets, developed after transfer to a matrix like Immobilon with specific antibodies to APP, Aβ and/or CD62 (as above); the antibody-labeled band is then visualized either by chemiluminescence or, if the antibody is isotopically labeled, by exposure of a photographic or X ray film; and c) ELISA, using solubilized activated platelets, then, after blocking and washing, specific antibodies to APP, Aβ and/or CD62 (as above), and detecting the bound antibody by alkaline phosphatase, biotin-avidin labeling, radioactivity, Kirkegaard reagent, etc., depending on the method and the labels attached to the primary or secondary antibodies.

Of these techniques, (a) is the most applicable to small numbers of platelets, as well as the easiest and the fastest. For these reasons, it is preferred for clinical laboratory applications. Most clinical laboratories have a flow cytometer (basically a single cell fluorescence detecting instrument, such as the Becton-Dickinson FAC Scan or comparable instruments sold by Coulter and others) which can be used to study the surface proteins on individual cells by binding a specific antibody to the cells, and detecting the amount of that antibody (as a measure of the protein) either by its direct fluorescence (if it is tagged with a fluorescent indicator) or by binding of a second antibody (which is fluorescently tagged) in a flow cytometer. To perform the assay method of this invention, these clinical laboratories could use a simple kit containing fluorescently tagged antibody to APP, as well as a pre-packaged Sepharose 2B minicolumn, buffers and thrombin; they would draw blood, obtain pure platelets after passing them through the Sepharose 2B, and compare the fluorescence of the antibody-bound platelets before and after thrombin stimulation.

EXAMPLES

In order to facilitate a more complete understanding of the invention, a number of Examples are provided below. However, the scope of the invention is not limited to specific embodiments disclosed in these Examples, which are for purposes of illustration only.

Example 1

Secretion by Activated Platelets

Platelet Isolation:

Platelets were prepared by Sepharose 2B chromatography from freshly drawn citrate-anticoagulated blood, as described in Davies, et al. (1993, 1996, incorporated herein by reference). Platelets were obtained from healthy young controls (C), normal age-matched volunteers (AM), Alzheimer's disease (AD) and Pick's disease patients, diagnosed as previously described (Davies, et al., 1993, 1996). The AD patients used in this study were all in the advanced stages of AD, and were in-patients in the Alzheimer's unit, a hospice, at the Bedford VA hospital. Approximately half of the patients included in these studies who have since died have been autopsied; the diagnosis of AD has been confirmed in all of these.

Blood for platelet separation was obtained, with appropriate approval from the relevant Institutional Review Boards, from 4 groups of donors: healthy young controls (C) (age range 20–47 yrs., mean age±standard deviation, 28.7±4.9, male/female ratio 13/12, n=25), non-demented age-matched volunteers (AM) (age range 50–79 yrs., mean 60.8±8.2, male/female ratio 10/7, n=17), patients from the Veteran Administration Hospital, Bedford, Mass., diagnosed as having probable AD by the Diagnostic and Statistical Manual of Mental Disorders criteria (age range 61–84 yrs, mean 70.5±5.4, male/female ratio 23/4, n=27, 20 of the 27 patients have died and 13 have been confirmed as AD on autopsy) or Pick's Disease patients (PD) (age range 62–75 yrs., mean 68.6±4.7, male/female ratio 5/1, n=6, 4 of the 6 have died and all 4 have been confirmed as PD on autopsy). The AD patients were all in advanced stages of the disease, mean duration 11±3.6 years, with a zero score on the Minimental State Examination score (Chui (1989), *Arch. Neurol.*, 46:806–814; Davies et. al., 1993; Davies, et. al., 1996).

The patients included in the present studies were medicated, if at all, only for seizures, a typical late stage AD-related occurrence, with low doses of Haldol or Dilantin. In order to verify that these medications did not directly adversely affect platelets or their function, platelets were incubated with these drugs at 4 and 20 ng/ml, respectively (doses yielding serum levels similar to those seen in the patient population) for 30 min. at 37° C.; under these conditions neither had any effect on the platelets' resting values or thrombin responses, although indirect effects in vivo on functions other than those measured here cannot be ruled out. Furthermore, neutrophils from the same patients were used as internal controls; their responses were normal for all donor groups, indicating that any differences found in platelet function were not due to a general blood abnormality.

The present studies confirm that no differences exist between the platelet's resting levels of intracellular $Ca^{++}_{in}$ {78.9±3.2 (n=29); 81.5±3.1 (n=24); 82.1±3.3 (n=28) nM} or their resting $pH_{in}$ {6.99±0.02 (n=35), 6.95±0.02 (n=28) 6.97±0.03 (n=30) for C, AM and AD, respectively}. The hyperacidification defect in platelets from patients with advanced AD was also confirmed {0.22±0.02 pH units, n=19 for AD, compared to AM or C, 0.14±0.01 pH units, n=14 and 0.15±0.02 pH units, n=19, respectively}.

Platelet Degranulation:

Platelet degranulation was monitored by measuring the amounts of granule contents secreted when the platelets were exposed to a 2× saturating (9 nM) dose of α-thrombin, using resting platelet values as baseline. The products whose secretion was measured included serotonin (from the dense granules) and β-glucuronidase (from the lysosomal granules), measured as described in Davies, et al. (1993). Thrombospondin, platelet factor 4 and N-terminal APP fragments secreted from α-granules was measured by ELISA. For ELISA assays, resting and activated platelet supernatants were prepared by centrifugation through 80:20 v/v Dow Corning Contour oil (2 min., 15,000 xg). Supernatants, diluted 1:1, were then loaded on microtiter plates and kept at 4° for 14–16 hours. After unbound sample removal, these plates were blocked with PBS containing 1% bovine serum albumin (BSA), labeled with mouse anti-human-thrombospondin (0.4 μg/ml), anti-platelet factor 4 (0.25 μg/ml), or anti-N-terminal APP (2 μg/ml)(22C11); following three washes, peroxidase-labeled goat anti-mouse or anti-rabbit IgG was added. TMB Microwell Substrate was used to develop the plates after thoroughly washing all wells. The reaction was stopped with 0.36N sulfuric acid and the absorbance read at 450 nm. Data were normalized to the response of control cells to 9 nM thrombin (100%). Analysis of variance and standard error of the mean (ANOVA) was used to determine the variance between donors.

Figure 1:
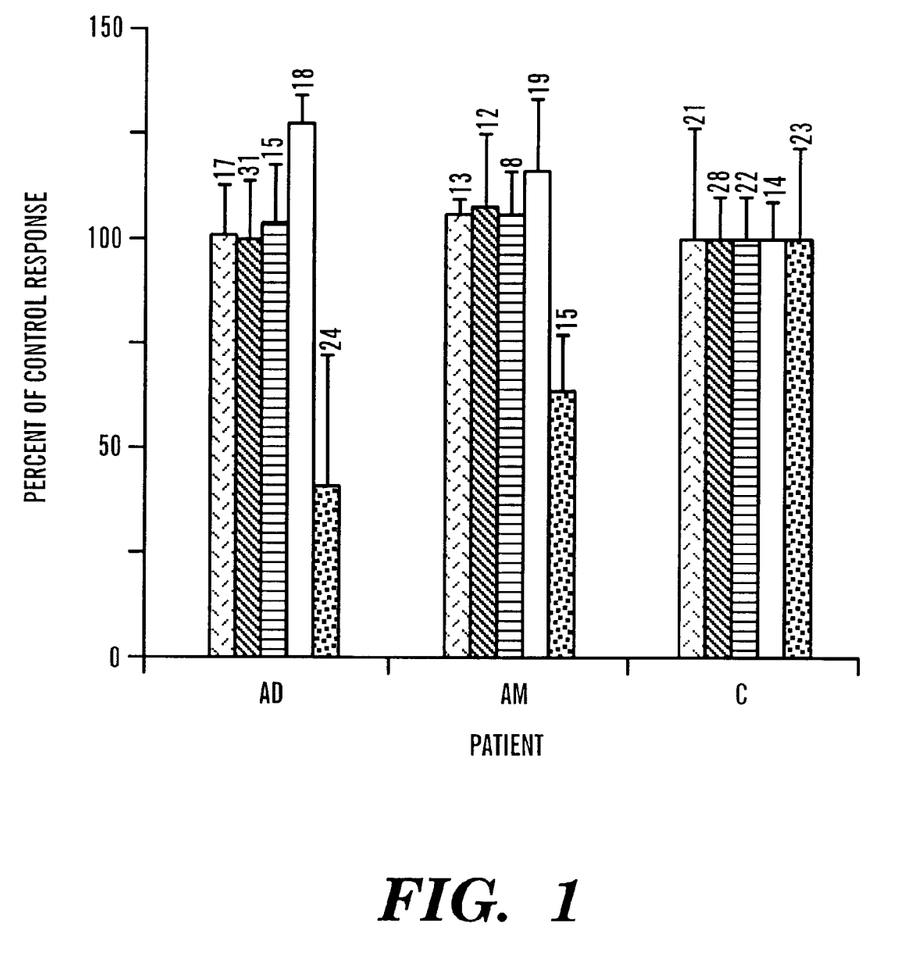
FIG. 1 is a bar graph showing secretion of soluble granule contents into the supernatant of activated platelets.

Secretion was monitored by measuring differences in secretion from resting and thrombin-stimulated platelets, and FIG. 1 shows the average differences for the soluble markers serotonin  and β-glucuronidase  and of thrombospondin , platelet factor 4  and N-terminal APP fragment . The numbers above each bar indicate the number of experiments, a total of 27 donors was tested with the same donor's platelets being tested 1–3 times.

The secretion of most, but not all, soluble granule contents after stimulation with a 2× saturating dose of α-thrombin (9 nM) was comparable from all three groups of platelets, as measured by serotonin for dense granules, by platelet factor 4, soluble APP and thrombospondin for α-granules, and by β-glucuronidase for lysosomal granules (FIG. 1). An exception was the secretion of soluble N-terminal containing fragments of APP which tended to be lower from both AD and AM platelets than from younger controls.

Example 2

Plasma Membranes of Activated Platelets

Membrane—Bound APP, CD62 and CD63 Measurements:

In addition to evaluation of the thrombin-induced platelet-secreted products detected in the supernatants of the activated platelets, two products translocated to the platelet plasma membrane by α-granules (CD62 and APP) and one from the lysosomal granules (CD63) were measured. The amount of membrane bound APP, CD62 and CD63 present on the membrane of resting and activated platelets 5 min. post-stimulation, was determined by flow cytometry on a FACS 440 flow cytometer (Becton Dickinson) with (a) a mouse monoclonal antibody to the N-terminal portion (22CI1, 10 μg/ml) or to the Aβ peptide region of APP (6E10, 10 μg/ml), followed by fluorescein-labeled goat anti-mouse IgG (1:500 dilution), (b) one of two rabbit polyclonal antibodies, prepared to residues 1–17 or 17–28, respectively, of Aβ (10 μg/ml each of pAb 1–17 and pAb 17–28), followed by a fluorescein-labeled goat anti-rabbit IgG (1:1000 dilution), (c) phycoerythrin-labeled CD62 (10 μl/test) and/or (d) fluorescein-labeled CD63 (10 μl/test). Fluorescence was detected with a 530/30 nm band pass filter and/or a 600 nm long pass filter and recorded with logarithmic scale amplification. Analysis of variance and standard error of the mean (ANOVA) was used to determine the variance between donors.

Figures 2A, 2C:
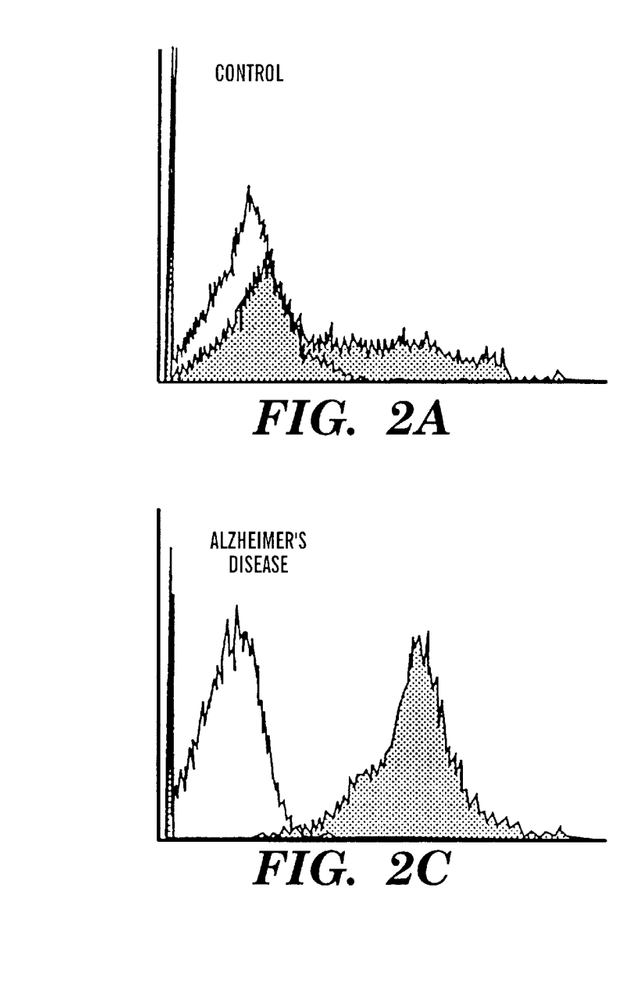
FIGS. 2A–2D show representative tracings of histograms indicating the amounts of membrane bound 22C11 recognized N-terminal epitope of APP on resting and thrombin-activated platelets from Alzheimer's disease (AD), Age-matched (AM), control (C), and Pick's disease (PD) donors.
Figure 2B:
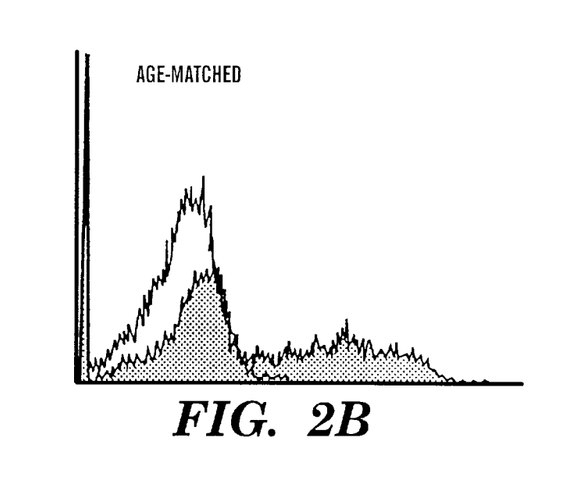
Figure 2D:
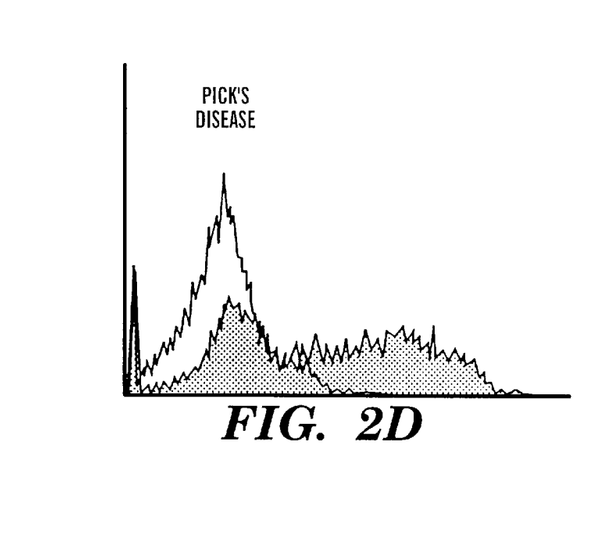
Figure 3A:
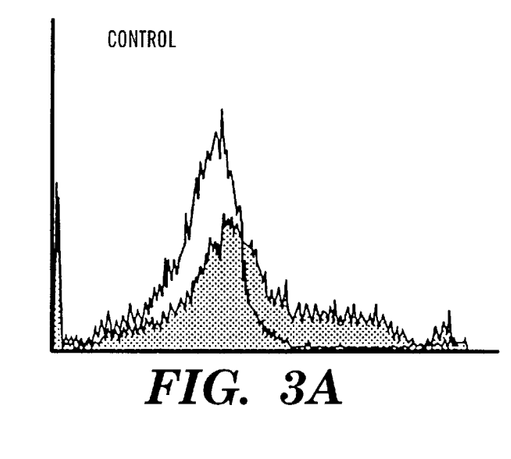
FIGS. 3A–3D show representative tracings of histograms indicating the amounts of membrane bound APP on resting and thrombin-activated platelets from AD, AM, C and PD donors (same experiment and donor's cells as in FIG. 2, labeled separately by polyclonal antibodies to residues 1–17 of the amyloidogenic Aβ fragment of APP).
Figure 3B:
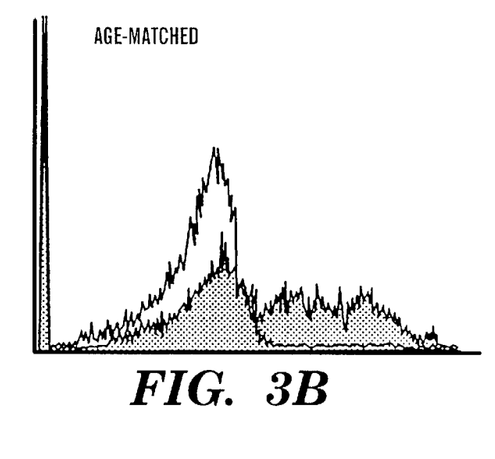
Figure 3C:
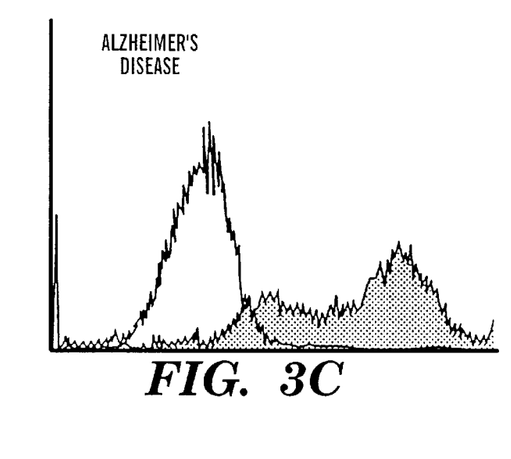
Figure 3D:
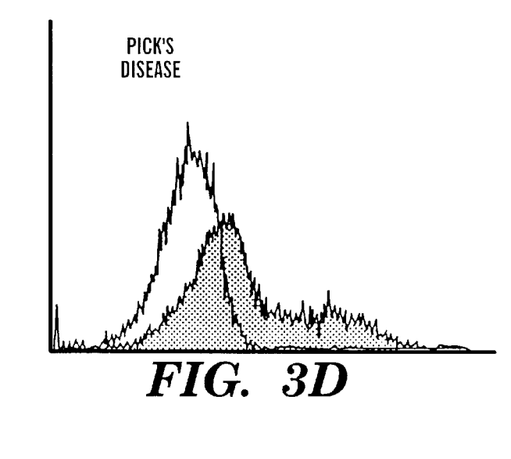
Figure 4:
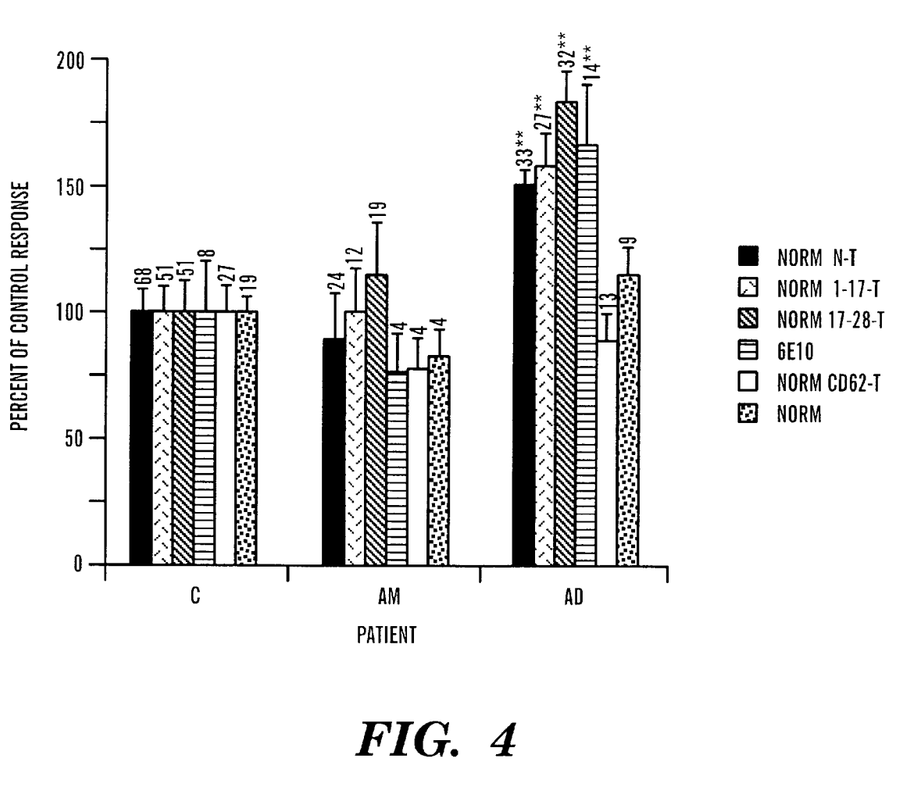
FIG. 4 is a bar graph showing retention of membrane proteins on activated platelets, measured as in FIGS. 2 and 3.

FIG. 2 shows the amount of membrane bound full length APP present on the membrane of resting [unshaded] and activated [shaded] platelets as determined by flow cytometry using an antibody to the N-terminal portion of APP (22C11). The y axis represents cell number, the x axis represents log fluorescence (proportional to amount) of antibody bound (as log $F_{530nm}$). FIG. 3 shows the amount of membrane bound Aβ present on the membrane of resting [unshaded] and activated [shaded] platelets, determined by flow cytometry using a polyclonal antibody to residues 1–17 of the Aβ portion of APP and a fluorescein-labeled goat anti-rabbit IgG; binding was monitored as in FIG. 2. FIG. 4 shows the average level of membrane proteins retained on activated platelet:. Surface proteins were measured as in FIGS. 2 and 3, using antibody 22C11  against N-terminal of APP and p1–17 , p17–28 , and 6E10  against Aβ peptide, and by fluorescein labeled CD62  and phycoerythrin-labeled CD63 , each added 5 min. post stimulation. Data were normalized to the response of control cells to 9 nM thrombin (100%). Analysis of variance and standard error of the mean (ANOVA) was used to determine the variance between donors; the numbers above each bar indicate the number of experiments, a total of 27 donors were tested with the same donor's platelets being tested 1–3 times. The * indicates statistical significance ($0.005<p<0.01$ to $0.01<p<0.025$, depending on the antibody and on donor variability).

Flow cytometry demonstrated (FIGS. 2–4) that there was a significant retention of translocated APP on the plasma membrane of platelets from AD but not on that from AM or C donors ($0.005<p<0.01$ to $0.01<p<0.025$, depending on the antibody and on donor variability). Four antibodies, mouse monoclonal anti-N-terminal APP (22C11) and anti-Aβ (6E10), and two rabbit anti-human antibodies to Aβ peptide residues 1–17 (1–17 pAb) and 17–28 (17–28 pAb), were used in these evaluations of mAPP in order to determine the form of the retained membrane bound protein (i.e. still containing the 22C11-recognized N-terminal epitope), had been cleaved at residue 1 of Aβ (i.e. the β secretase cut), or at residue 17 (i.e. the α-secretase intra-Aβ-peptide cut) (Esch, et al. (1990), *Science,* 248:1122–1124; Haass, et al. (1993), *Cell,* 75:1039–1042, incorporated herein by reference). Polyclonal antibodies to residues 1–17 and 17–28 of Aβ were prepared and affinity purified, utilizing affinity columns loaded with the respective peptide. Their specificities were determined by competitive ELISA (Table 1) in which specific recognition to each peptide and to the 1–40 Aβ fragment was evaluated. The antibodies did not cross-react with the opposite peptide, nor with a 1–40 mis-sense peptide, but each did recognize Aβ.

TABLE 1

Characterization of polyclonal antibodies to residues 1-17 (12Ab 1-17) and 17-28 (PAb 17-28) of AB by competitive ELISA.
The specificities of polyclonal antibodies pAb 1-17 and pAb 17-28 were determined by competitive ELISA. Plates were coated with β-amyloid peptide to residues 1-17, 17-28, 1-28, 1-14 or 12-28 which were coupled to BSA to facilitate attachment of the peptide to the ELISA plate. Antibodies, affinity purified using peptide coupled to Sulfo-Link gel, were then used to probe for bound peptide.

| Affinity purified 12Ab 1-17 | | Affinity purified 12Ab 17-28 | |
|---|---|---|---|
| Peptide Name | Titer | Peptide Name | Titer |
| 1-17 | 17,100 | 1-17 | <50 |
| 17-28 | <100 | 17-28 | 24,355 |
| 1-40 | 12,840 | 1-40 | 11,280 |
| 1-28 | 21,560 | 1-28 | 17,030 |
| 12-28 | 2,970[a] | 12-28 | 21,900 |
| mis-sense | <50 | mis-sense | <50 |

[a]most of the immunoreactivity resides in residues 1-11

FIGS. 2 and 3 show representative data (1 of 8 to 68, similar experiments, depending on the antibody used) of platelets surface labeled with anti-APP and anti-Aβ antibodies identified by flow cytometry; FIG. 4 summarizes the results. Data using 22C11 are shown in FIG. 2, those obtained using pAb17–28 are shown in FIG. 3, those obtained using all four antibodies (pAb 1–17 and pAb17–28 and mAb 6E10 and mAb22C11) are shown in FIG. 4, demonstrating that the results were comparable with all antibodies utilized. Additionally, we found no differences in the translocation of CD62 and CD63 (FIG. 4), confirming that the APP processing defect observed is specific for AD patients and is not part of a more generalized problem with the platelet's alpha or lysosomal secretion.

Example 3

Specificity to Alzheimer's Disease

Patients with PD exhibit a dementia whose clinical presentation is very similar to AD, but whose neuropathology shows Pick bodies (Chui (1989), *Arch. Neurol.,* 46:806–814). Platelets from patients diagnosed with Pick's disease were treated as described in Example 2, and data representative of 3 Pick's Disease (PD) patients are included in FIGS. 2 and 3. While PD platelets do exhibit the hyperacidification defect in response to thrombin, they do not retain APP on the activated platelets' plasma membrane. Therefore Pick's disease patients do not appear to have the APP processing defect reported here for AD. The results demonstrate that the retention of APP on the activated platelet surface is specific to platelets from patients with AD, but apparently not related directly to their hyperacidification defect.

Example 4

Characterization of Plasma membrane APP

In order to determine if the retained APP on membranes of activated AD platelets is full length APP or APLP (a protein identified in some cells which strongly resembles the sequence of APP but lacks the Aβ domain (Wasco, et al. (1993), *Nature Genetics,* 5:95–100), the relative ratios of the bound anti-N-terminal (22C11) to bound anti-Aβ region (pAb 1–17, pAb 17–28 or 6E10) antibodies were calculated. If there were APLP present, which lacks Aβ, the anti-Aβ antibodies would not bind and the relative amounts of mAb22C11-recognized mAPP versus pAb 1–17- and pAb 17–28-recognized mAPP should change dramatically. Conversely, if there were cleavage within the retained APP, there should be less anti-N-terminal (22C11)-recognized APP and more pAb 1–17- and pAb 17–28-recognized APP bound. The observed data fit neither of these possibilities; i.e. the ratio for the three antibodies was similar for each donor group. Therefore, the mAPP retained on the patients' activated platelets was neither APLP nor was it partially processed.

Western Blot Analysis of Platelet Samples

Figure 5:
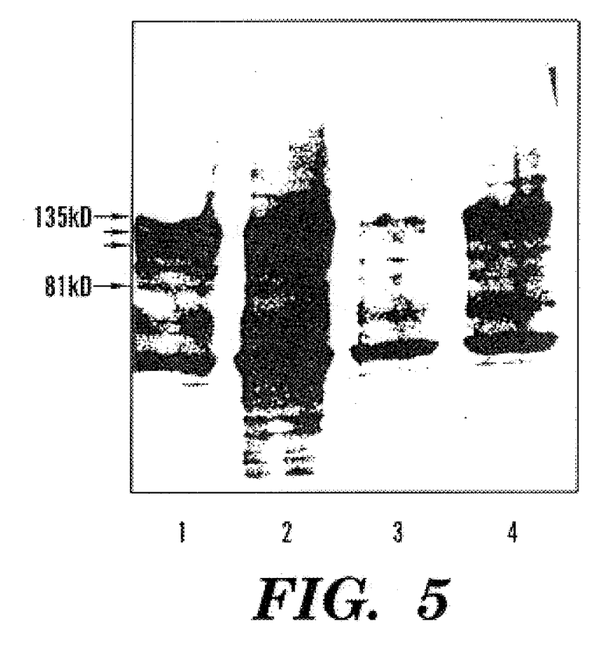
FIG. 5 shows Western blots of resting and stimulated platelet pellets from control (C) and Alzheimer's disease (AD) donors with monoclonal antibody 22C11.
Figure 6:
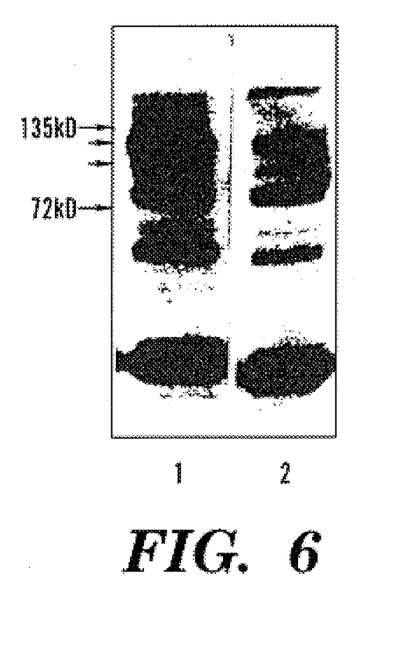
FIG. 6 shows Western blots of stimulated platelet supernatants from C and AD donors with monoclonal antibody 22C11.

Western blots of resting and activated platelet pellets from C and AD donors were performed in order to confirm the existence of the proteolytic defect in patients with AD. Pellets and supernatants from resting and thrombin-stimulated platelets were analyzed by Western blotting. Samples were electrophoresed on 4–20% gradient or 7.5% SDS mini gels and transblotted to Immobilon utilizing a semi-dry system. Development followed with a monoclonal antibody to the N-terminus of APP (22C11). Visualization was accomplished by Enhanced Chemiluminescence (ECL). FIGS. 5 and 6 show, respectively, activated platelets and their concentrated supernatants (from the same donor). Either solubilized activated platelets (FIG. 5) or their concentrated supernatants (FIG. 6) were electrophoresed on a 4–20% gradient gel and Western blotted with monoclonal antibody 22C11.

FIG. 5 shows pellets from resting (lanes 1 and 2) and stimulated (lanes 3 and 4) platelets, electrophoresed on a 4–20% gradient gel and Western blotted with monoclonal antibody 22C11. The figure shows controls (lanes 1 and 3) and AD patients (lanes 2 and 4) respectively. FIG. 6 shows Western blots of concentrated supernatants from platelets stimulated with 9 nM thrombin, electrophoresed on a 4–20% gradient gel and Western blotted with monoclonal antibody 22C11. The figure shows controls (lane 1) and AD patients (lane 2), respectively.

As shown in FIG. 5, resting platelet pellets from control and AD patients contain comparable amounts of 22C11 recognized N-terminal epitope of APP (lanes 1 and 2) (gels normalized with equal amounts of protein). Upon activation, a considerable amount of mAb22C11-recognized APP was lost from the control platelets (lane 3) but was retained by platelets from patients with AD (lane 4). Platelets from AM donors resulted in results similar to control donors (data not shown). As would be expected, Western blots of concentrated platelet supernatants from the control and AD patients showed that activated control platelets had released markedly more soluble APP fragments (FIG. 6). These data therefore corroborate that an APP processing defect in platelets from AD patients exists, resulting in reduced soluble APP release (FIGS. 1 and 6) and increased APP retention (FIGS. 2–5).

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in medicine, neurology, immunology, hybridoma technology, pharmacology, and/or related fields are intended to be within the scope of the invention, which is limited only by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

We claim:

1. A method for screening samples to aid in diagnosis of Alzheimer's disease in a patient, comprising the steps of:
   a) inducing degranulation of platelets obtained from a blood sample of the patient;
   b) measuring the amount of amyloid precursor protein (APP) attached to the plasma membrane of the degranulated platelets by incubating the degranulated platelets of step a) with a first antibody which specifically binds to an APP epitope and detecting the presence of the antibody specifically bound to the degranulated platelets; and
   c) determining whether the amount of APP attached to the plasma membrane of degranulated platelets from the patient is greater than the amount of APP attached to the plasma membrane of degranulated healthy age-matched control platelets, a determination that the amount of APP attached to the plasma membrane of the degranulated platelets from that patient is greater than the amount of APP attached to the plasma membrane of degranulated healthy age-matched control platelets being indicative of a diagnosis of Alzheimer's disease.

2. The method of claim 1, wherein the antibody specifically binds amyloid β-peptide.

3. The method of claim 1 wherein the first antibody is labeled and the detection of step b) comprises detecting the label.

4. The method of claim 1 wherein the specific binding of the first antibody is detected using a second detectably labeled anti-Ig antibody which specifically binds the first antibody.

5. The method of claim 3, wherein the label comprises a fluorescent moiety.

6. A method for screening samples to aid in diagnosis of Alzheimer's disease in a patient, comprising the steps of:
   a) providing a sample containing platelets from the blood of patient;
   b) activating platelets obtained from the patient;
   c) determining the amount of amyloid precursor protein (APP) attached to the outer membrane of the activated platelets of the patient, an increase in the amount of APP attached to the outer membrane of the activated platelets of the patient compared to the average amount of APP attached to the outer membrane of the activated platelets of healthy, age-matched control persons being indicative of Alzheimer's disease in the patient.

7. A method for screening patients for Alzheimer's disease, comprising the steps of:
   a) inducing degranulation of platelets from a sample of blood obtained from the patient;
   b) separating degranulated platelets from the proteins secreted by degranulation;
   c) labeling the outer membrane of degranulated platelets with a labeled composition which specifically binds to at least a portion of amyloid precursor protein (APP); and
   d) determining the amount of label which specifically binds amyloid precursor protein (APP) attached to the outer membrane of the degranulated platelets of the patient, a determination that the amount of label which specifically binds APP attached to the outer membrane of the degranulated platelets from that patient is greater than the amount of APP attached to the outer membrane of degranulated healthy age-matched control platelets being indicative of a diagnosis of Alzheimer's disease.

* * * * *